(12) United States Patent
Jenkins

(10) Patent No.: US 7,777,157 B2
(45) Date of Patent: Aug. 17, 2010

(54) PORTABLE BLANKET WARMER

(75) Inventor: Casey Jenkins, Elizabethtown, KY (US)

(73) Assignee: Life Gear LLC, Elizabethtown, KY (US)

( * ) Notice: Subject to any disclaimer, the term of this patent is extended or adjusted under 35 U.S.C. 154(b) by 827 days.

(21) Appl. No.: 11/636,779

(22) Filed: Dec. 11, 2006

(65) Prior Publication Data

US 2008/0149614 A1    Jun. 26, 2008

(51) Int. Cl.
*F24C 7/10* (2006.01)
(52) U.S. Cl. .................. 219/386; 219/227; 219/533
(58) Field of Classification Search ............. 219/386, 219/385, 212, 214, 521, 227, 533
See application file for complete search history.

(56) References Cited

U.S. PATENT DOCUMENTS

| | | | |
|---|---|---|---|
| 1,659,719 A * | 2/1928 | Blake | 219/385 |
| 3,385,952 A * | 5/1968 | Mix | 219/387 |
| 3,624,346 A * | 11/1971 | Guth | 219/201 |
| 3,746,837 A | 7/1973 | Frey et al. | |
| 3,989,924 A * | 11/1976 | Kurtzer | 219/211 |
| 4,163,896 A | 8/1979 | McAvinn et al. | |
| 4,481,410 A * | 11/1984 | Bortnick | 219/521 |
| 4,523,078 A | 6/1985 | Lehmann | |
| 5,183,994 A * | 2/1993 | Bowles et al. | 219/387 |
| 5,397,815 A * | 3/1995 | Carlin | 523/332 |
| 5,615,604 A * | 4/1997 | Chenglin | 99/332 |
| 5,736,714 A * | 4/1998 | Bechtold, Jr. | 219/521 |
| 5,981,909 A * | 11/1999 | Freeman | 219/386 |
| 6,723,960 B2 | 4/2004 | DiMartino et al. | |
| 7,161,120 B1 * | 1/2007 | Stroud et al. | 219/386 |
| 7,230,212 B1 * | 6/2007 | Sarkisian et al. | 219/521 |
| 2006/0027557 A1 | 2/2006 | Peterson et al. | |

* cited by examiner

*Primary Examiner*—Thor S Campbell
*Assistant Examiner*—Vinod D Patel
(74) *Attorney, Agent, or Firm*—Stockwell & Smedley, PSC

(57) ABSTRACT

A blanket warmer is disclosed. The blanket warmer is lightweight, portable, and consumes minimal power.

25 Claims, 10 Drawing Sheets

US 7,777,157 B2

PORTABLE BLANKET WARMER

CROSS REFERENCE TO RELATED APPLICATIONS

This application claims priority to International Application No. PCT/US2006/41619, filed on Oct. 25, 2006, which in turn claims priority to U.S. Provisional Application No. 60/731,606, which was filed on Oct. 31, 2005.

FIELD OF THE INVENTION

This invention relates generally to a blanket warmer. More specifically, this invention relates to a blanket warmer which is lightweight, portable, and consumes a minimum of power.

BACKGROUND OF THE INVENTION

For a variety of reasons there is always a need for a person to warm himself or herself by covering their body with a blanket. Most hospitals currently provide warm blankets to their patients. The ability for an individual to access a heated, non-corded, blanket whenever they need one will increase the comfort of that individual. Consequently, an improved means of warming blankets is desired.

SUMMARY OF THE INVENTION

It is the object of this invention to temporarily raise the temperature of a standard household blanket. It is another object of this invention to raise that temperature in an efficient manner, that does not consume large amounts of power. These and other objects and advantages of the invention will become readily apparent as the following description is read in conjunction with the accompanying drawings.

DETAILED DESCRIPTION OF THE PREFERRED EMBODIMENTS

Before explaining the disclosed embodiment of the present invention in detail it is to be understood that the invention is not limited in its application to the details of the particular arrangement shown, since the invention is capable of other embodiments. Also, the terminology used herein is for the purpose of description and not of limitation.

Figure 1:
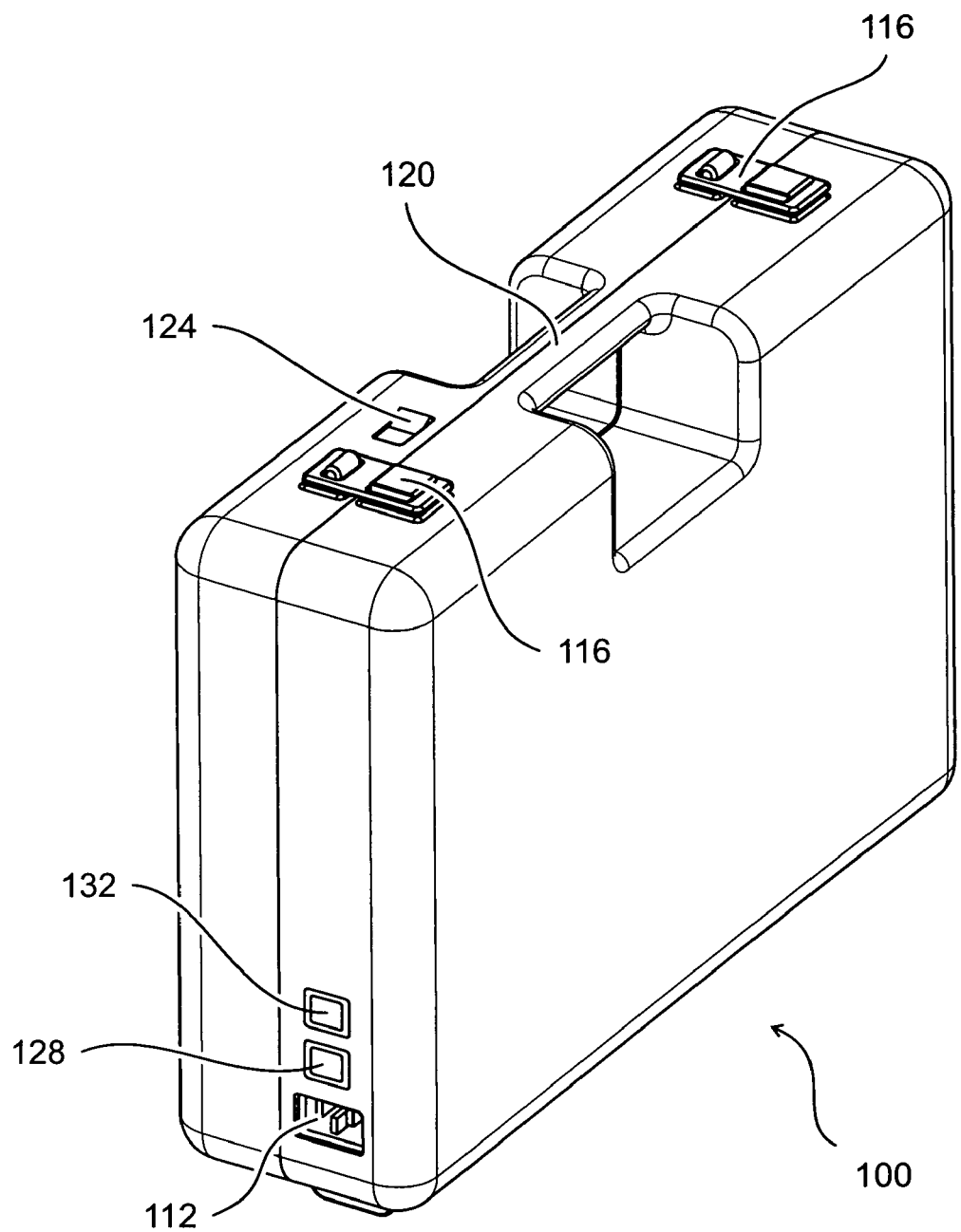
FIG. 1 shows the blanket warmer of the present invention in a closed position.

As shown in FIG. 1, the blanket warmer 100 of the present invention comprises a small portable/mountable container capable of warming and storing one and possibly two blankets. The blanket warmer 100 can be energized from either a 110-volt electrical outlet 112, a DC converter (not shown in FIG. 1), or directly from the electrical system used in a vehicle such as an automobile or helicopter. The blanket warmer's small size and shape make it useful for a potential seat, and its exterior design may allow for other convenient features, such as advertising.

Also as shown in FIG. 1, the blanket warmer 100 has latches 116 and an on-off switch 124. The body of the blanket warmer 100, when in its closed position as shown in FIG. 1, comes together to form a handle 120. The switch 124 can be of a rocker type, and can have a light or indicator embedded therein to show when the blanket warmer 100 is presently drawing power.

As shown in FIG. 1, the lower case 104 and upper case 108 have a latch 116 located on their closing area. The latches 116 allow for the holding closed of the case assembly for the purposes of heating the blankets, and also for carrying the heated blankets.

However, as stated, the latches 116 also have electrical features such that the circuit is enabled when the upper and lower portions 104, 108 are pressed together and the latches 116 are closed. The electrical capability is designed so that electrical connection at the switch 124 can only occur while the case is closed in the correct position. Only when the case assembly has been closed and latched will the switch 124 allow electrical current to flow. This way, no power flow can occur when the blanket warmer 100 is open.

Figure 2:
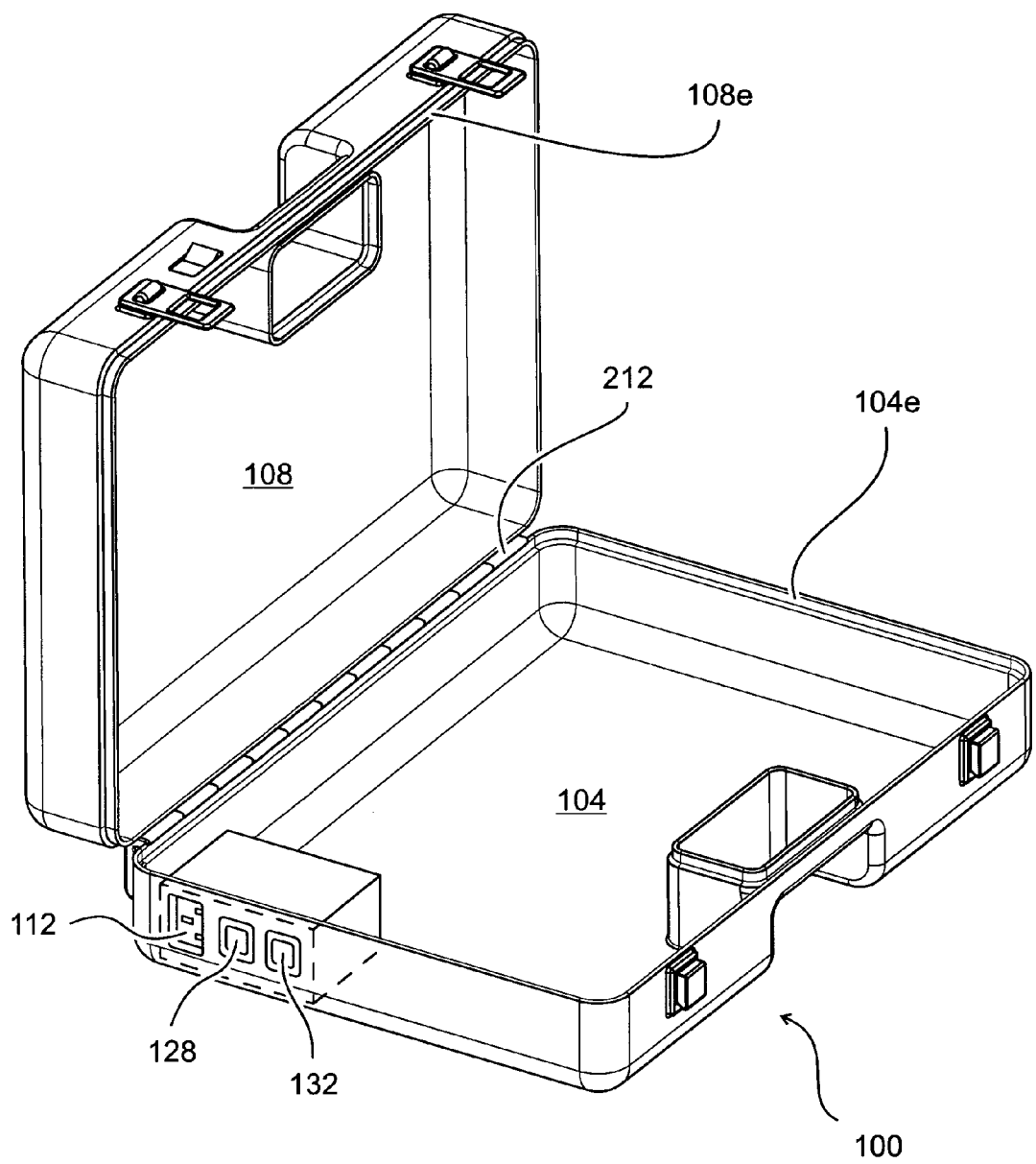
FIG. 2 shows the blanket warmer of FIG. 1 in an open position.
Figure 7:
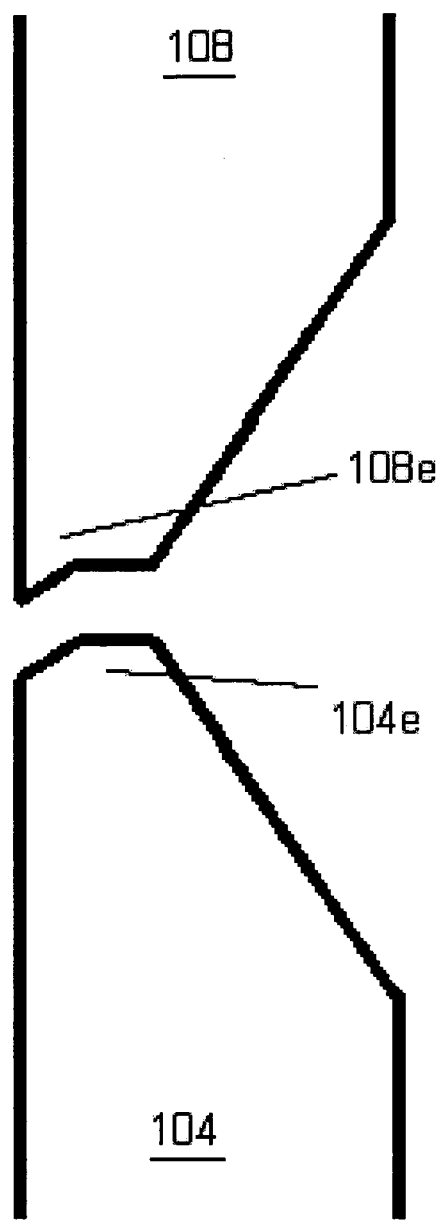
FIG. 7 shows a detailed view of a portion of the present invention.

FIG. 2 shows the body of the blanket warmer 100, where the upper portion 108 is joined to a lower portion 104 by a hinge 212. The hinge 212 can be full length, but can also be in other configurations. The edge of the upper portion is designated 108e, and meshes with the edge 104e of the lower portion at an angle, as shown in FIG. 7. This effectuates an effective insulating quality for the blanket warmer 100.

As shown in FIGS. 1 and 2, when the interior of the blanket warmer 100 has reached a desired temperature, an "in use" indicator 128 can be enabled. When the blanket warmer 100 has reached its maximum temperature, it can also illuminate a "blanket fully heated" indicator 132. Within the blanket warmer 100 of the present invention, one such optimum temperature of a blanket could be from 35-50° C., although this range is but exemplary, and the present invention should not be considered as limited exclusively thereto. Also, other means of indicating the status of the blanket warmer 100 are contemplated with the spirit and scope of the present invention, including multicolored indicator lights and/or embedding single or multiple indicators within the switch 124.

Figure 3:
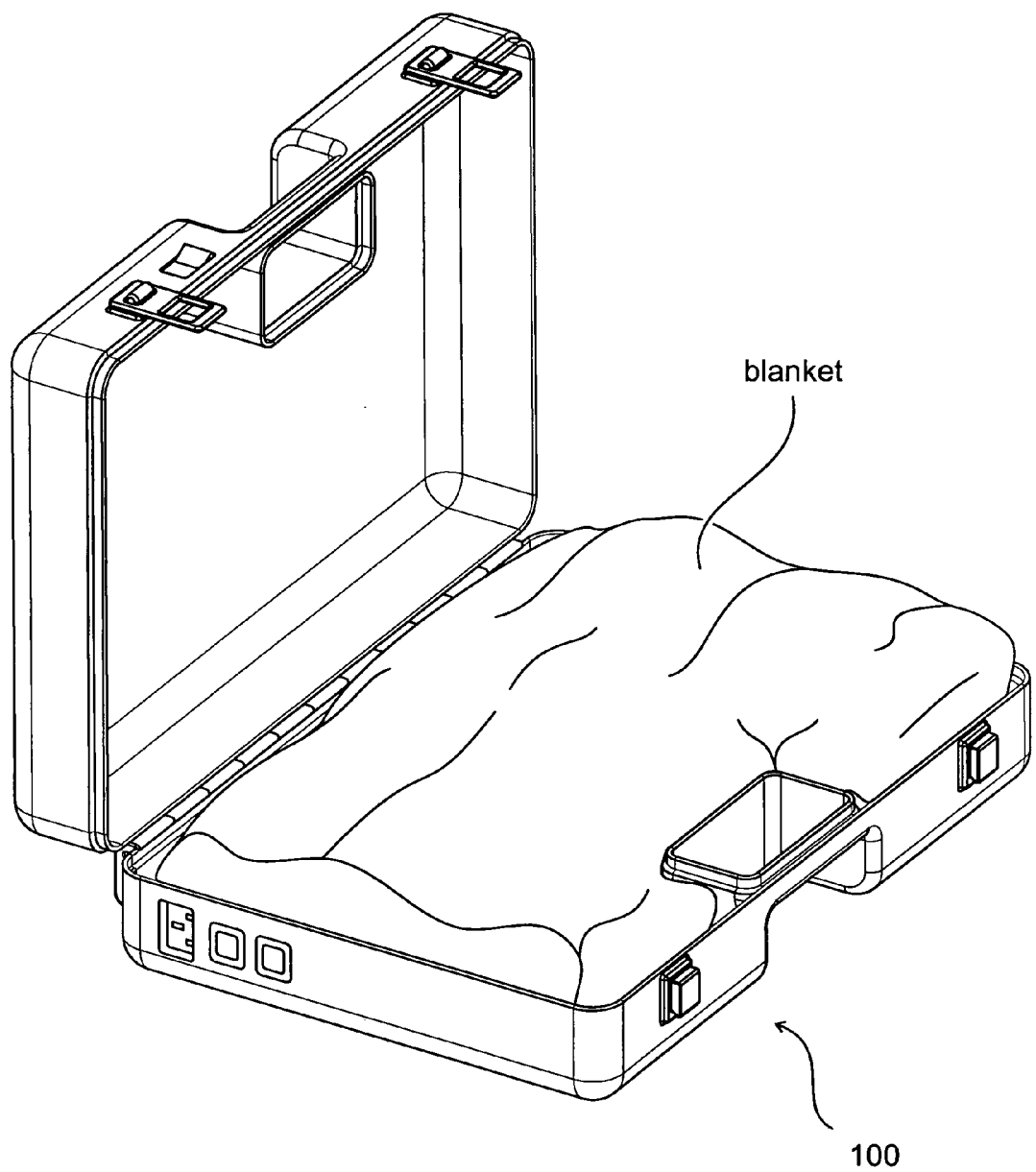
FIG. 3 shows the blanket warmer of FIGS. 1 and 2 with a blanket contained therein.

FIG. 3 shows a single blanket occupying the interior of the blanket warmer 100. To operate the blanket warmer 100 of the present invention, it is not necessary that the blanket be neatly arranged, and it is even possible to operate the blanket warmer where a small portion of the blanket is not entirely contained within the body cavity of the blanket warmer 100.

Figure 4:
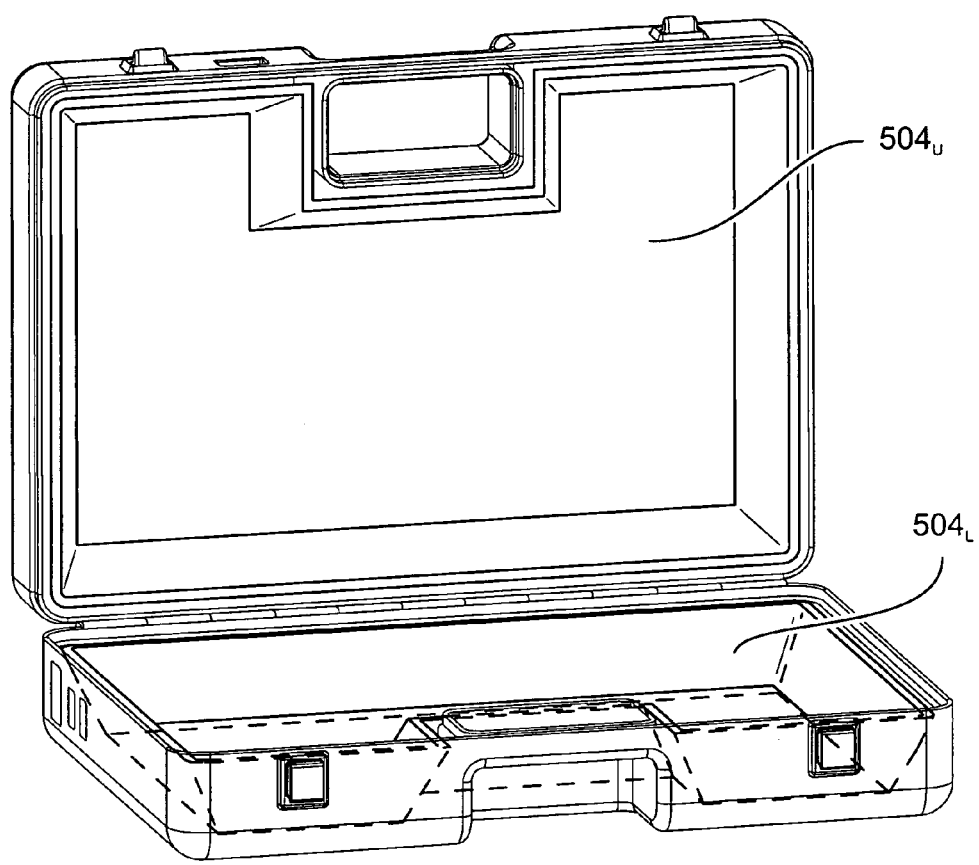
FIG. 4 shows a wiring harness for use within the present invention.
Figure 5:
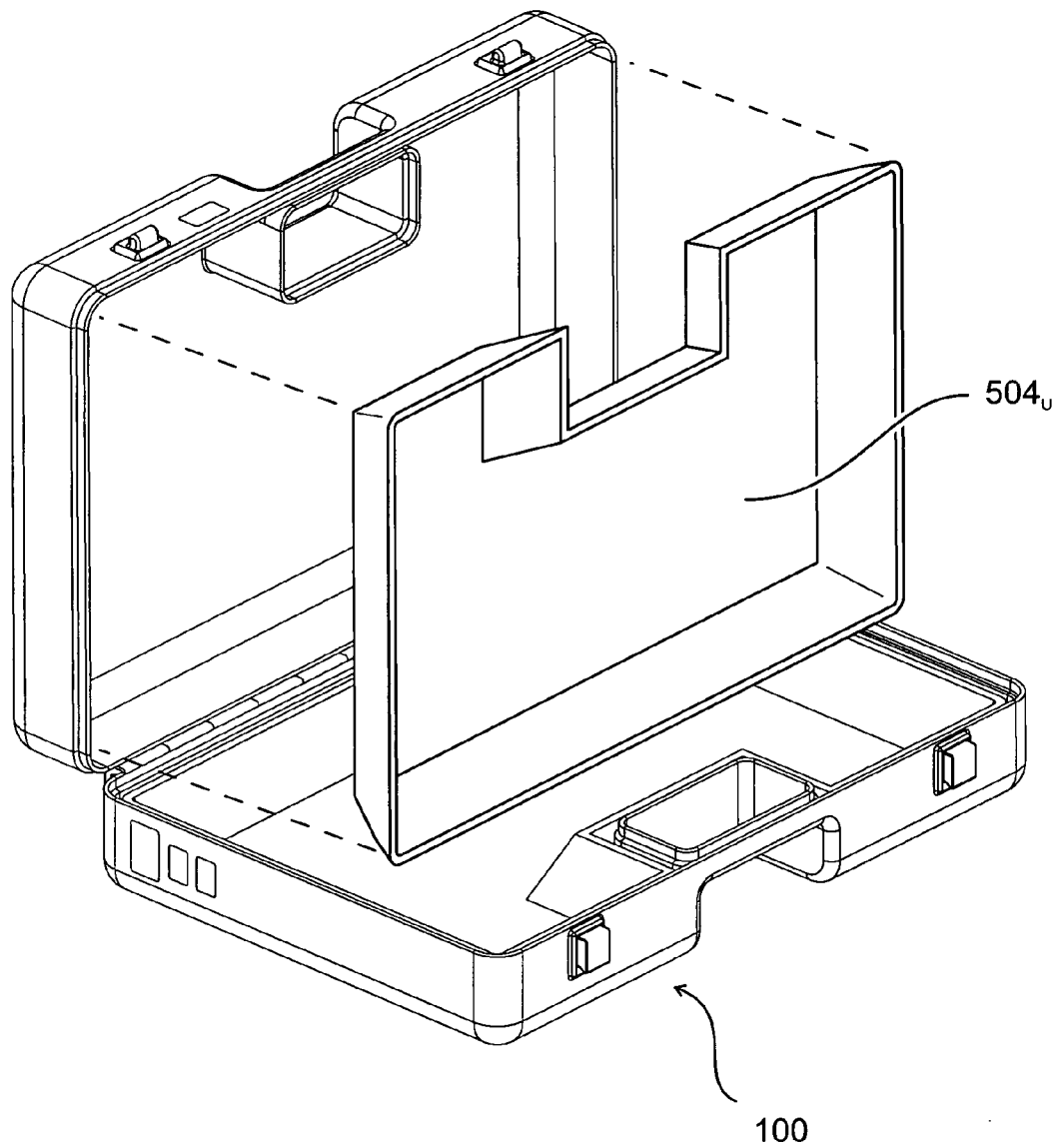
FIG. 5 shows a liner for use within the present invention.
Figure 6A:
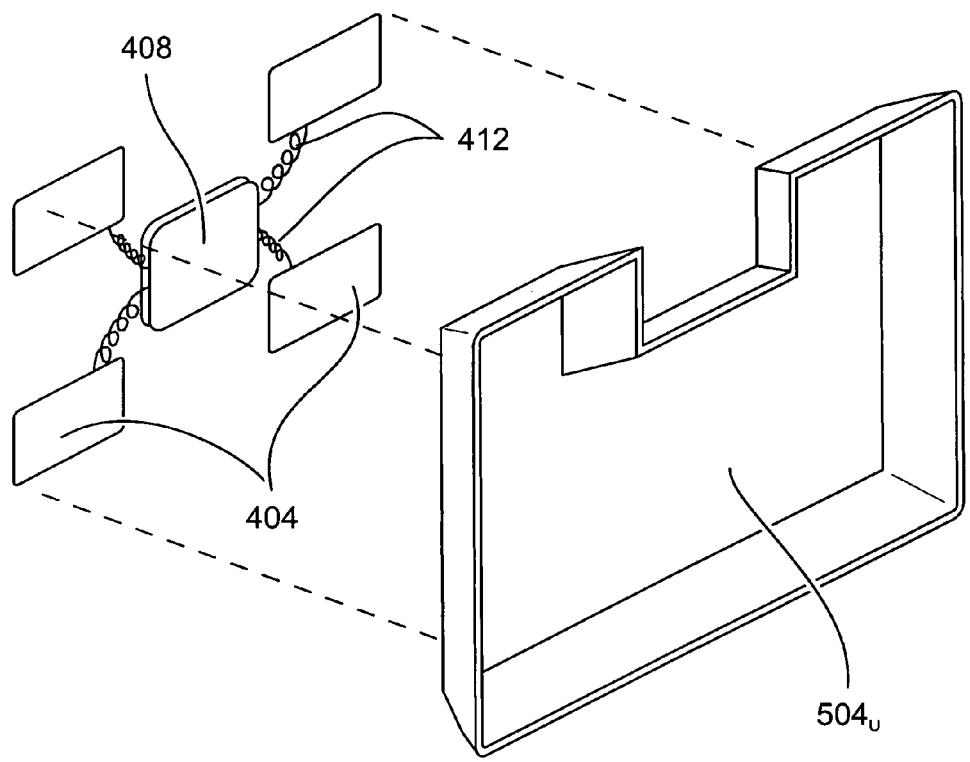
FIGS. 6A & 6B show exploded views of the assembly of the present invention.

FIGS. 4 and 5 show separate liners $504_U$ and $504_L$, which are located inside the upper portion 108 and lower portion 104 respectively. FIG. 6A shows specific detail of the wiring harnesses 412U and 412L of the present invention, where the U and L connote Upper and Lower, respectively. The heating elements 404 can reach a maximum temperature of 80° C., and are regulated by the temperature sensors 408U and 408L. If the temperature sensor 408 determines that a wiring harness 412 (either Upper or Lower) is about to rise above a predetermined temperature, such as but not limited to 80° C., the sensor 408 will disable that wiring harness. Similarly, if a temperature sensor 408 determines that a wiring harness (either Upper or Lower) is about to fall below a predetermined temperature, such as but not limited to 72° C., the sensor 408 will enable that wiring harness.

The temperature sensors 408 can be of a bi-metal type, where two different pieces of metal heat at a different rate. As the two pieces of metal heat up, a curling effect occurs between them. Eventually, at a predetermined temperature, the two pieces physically separate, so that any electrical circuit passing therethrough is broken. The latches 116 also act to close the electrical circuit and enable the wiring harnesses 412 to function. If the latches 116 are not engaged, the electrical circuit remains open and unconnected.

Figure 6B:
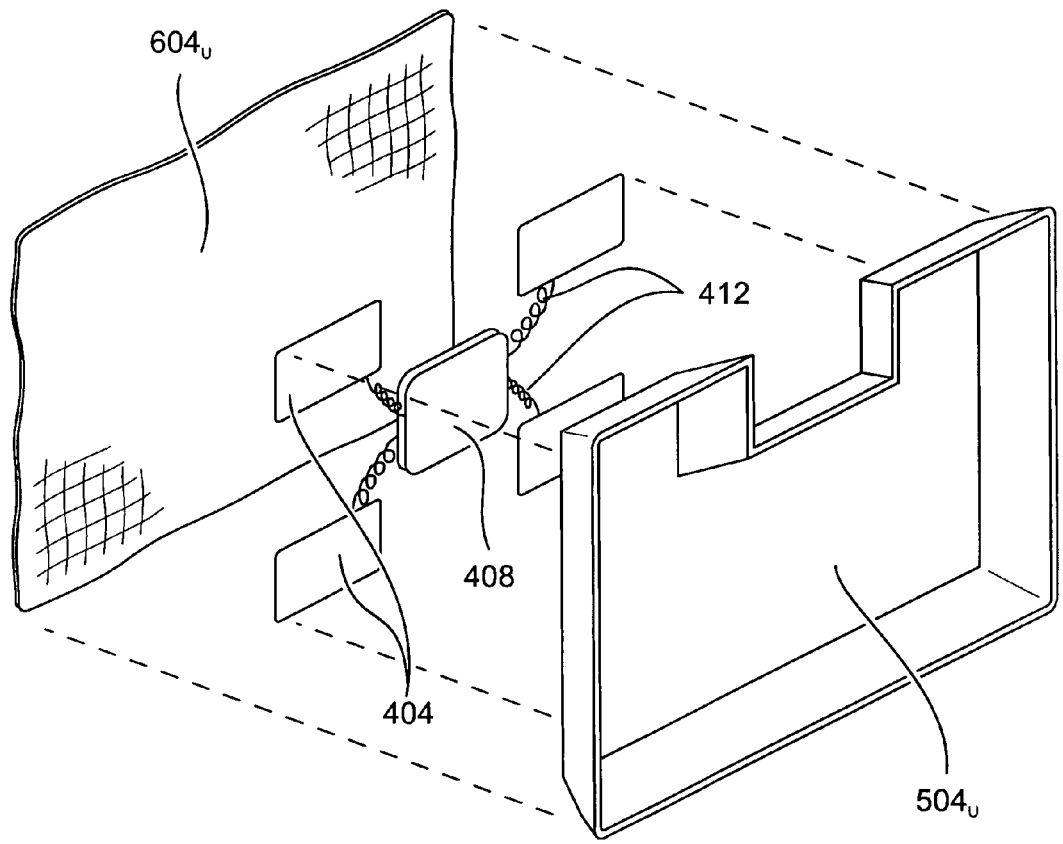

The arrangement of wiring harnesses 412 of FIGS. 6A and 6B are but for exemplary purposes only, so that the present invention should not be considered as limited exclusively thereto. The heating elements 404 within the wiring harness 412 can be arrayed in and composed of a variety of configurations. Specifically, rather than the four elements 404 shown per harness 412, there could also be two, eight or some other number of heating elements. Accordingly, the present invention should not be considered as limited to a specific number, physical arrangement, or temperature range of heating elements, so that any embodiment shown herein is for illustrative purposes only.

As shown in FIG. 6A, the liners 504 attach directly to the heating elements 404, and transfer the heat uniformly to the blanket in such a way that the transferred heat is diffused and non-localized. Because the liners 504 dissipate the heat from the elements 404 uniformly across their entire surface area, localized or non-uniform heating is avoided. In other words, the blanket warmer 100 contemplates and addresses a situation where a blanket may be wadded or bunched to have a non-uniform thickness while inside. The present invention can still ensure that heat transfer from the liners 504 to the blanket occurs in a relatively uniform fashion. Additionally, the liners 504 are specifically manufactured to be formed from a material that lends itself well to transferring heat through their entire surface, regardless of the fact that the heat-energy might be derived from a localized source.

One material that is suitable for such uniform heat transfer is aluminum. Aluminum is chosen because it dissipates heat very effectively and uniformly. However, the liners 504 can be composed of other materials besides aluminum. The liners 504 can also be painted or coated with a material that lends itself well to transferring and not retaining heat. After all, the purpose of the liners 504 is not to get hot themselves, but to transfer heat energy to the blanket. Within the liners 504, after a predetermined period of time, the heat conduction is uniform.

The liners 504 and the outside body of the blanket warmer 100 could also be equipped with air-holes. This would only be for an embodiment which heats partly by convection. However, the embodiments shown in FIGS. 4-6 heat more by conduction and radiation than by convection.

From FIGS. 4-6 it is apparent that the liners 504 are not strictly rectangular, but are angled. This is useful to direct a blanket to the center of the device, and concentrate the blanket so that more blanket surface area is available for contact with the surface of the liners 504.

The outer body of the blanket warmer 100 can be composed of a high rigidity heat resistance plastic or fiberglass, such as but not limited to acrylonitrile butadiene styrene. Alternatively, it could be composed of stainless steel, wood, or other material having suitable moldability and adaptability for fabrication and manufacturing. In any case, the composition must have insulating qualities, as the task of the blanket warmer 100 is, as stated, to transfer heat to the blankets therein, and not to heat itself. Thus, from the outside, the body/chassis of the blanket warmer 100 should not be noticeably warmer when in use. A user will discern that a blanket is completely heated by viewing the indicator lights of the present invention, such as but not limited to lights 128 and 132, as opposed to touching the body/chassis of the blanket warmer 100.

FIG. 6A shows one possible way in which the blanket warmer 100 of the present invention can be assembled. However, other possible manufacturing arrangements are also contemplated within the spirit and scope of the present invention. The wiring harnesses 412 can first be attached to the liners 504.

Meanwhile, as shown in FIG. 6B, an isolating layer 604 is located between the wiring harnesses 412 and the inner surface of the outer body of the blanket warmer 100. Because the example in FIG. 6B is meant to fit with the upper portion 104, the isolating layer is labeled $604_U$. The isolating layers 604 can be made, for example, from aluminum silicate fire resistant insulated material, although other compositions are possible. The isolating layers 604 can also be manufactured in sheet form for convenient separation into the sizes useful for fitting directly inside the present invention. The isolating layers 604 can either be attached directly to the inner surface of the outer body, or can be attached to the liners 504 after the wiring harnesses 412 are installed therein. Accordingly, FIG. 6B is shown for exemplary purposes only. In either case, the isolating layer has the effect of preventing any portion of the electrical features of the present invention, including the wiring harnesses 412, from accidentally grounding to the outer body of the blanket warmer 100.

After the wiring harnesses 412 are attached to the liners 504, the overall assembly can then be welded or pop-riveted to the interior surface of the outer body of the blanket warmer 100. Also, the components of the wiring harnesses 412 are chosen to be as fool-proof as possible, to reduce if not outright eliminate the possibility of an assembler making some type of assembly error.

As stated, FIG. 7 shows a detailed view of the edges 504e and 508e. These angles are calibrated to achieve maximum heating utility, even when a portion of the blanket is not trapped entirely inside the blanket warmer 100. As stated, the liners 504 are also angled so as to direct the bulk of the blanket toward the center of the device.

Figure 8:
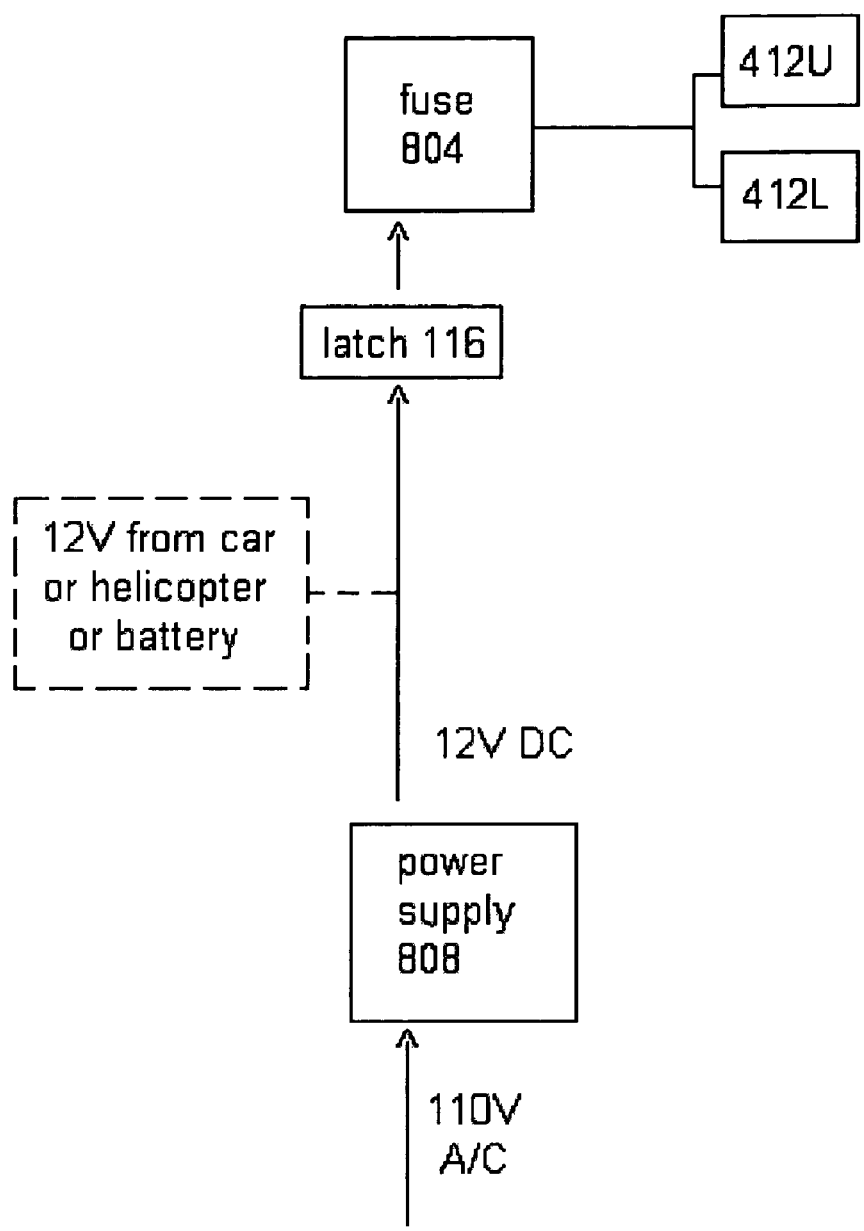
FIG. 8 shows a wiring diagram of the present invention.

FIG. 8 shows a wiring diagram of the present invention. The wiring harnesses 412 controls the heating of the assembled unit 100 by opening and closing the circuit when needed to maintain the correct temperature, as determined by the temperature sensors 408. As shown in FIG. 8, a fuse 804 also exists in case the wiring harnesses 412 are drawing too much current and thus rising above a predetermined temperature, such as (but not limited to) 85° C. As shown in FIG. 8, this fuse 804 is located between the power supply 808 and the wiring harnesses 412. The latches 116 can also act to break the circuit and cut power.

As shown in FIG. 8, the blanket warmer 100 of the present invention can be implemented so that 110 volt AC electricity is converted into 12 volts DC. This is so as to be compatible with the power supplied directly from an automobile, a helicopter (such as a Medi-Vac), or a boat's electrical system. Alternatively, a battery back can also be employed, which could be useful for situations where no AC electric outlets are convenient.

Figure 9:
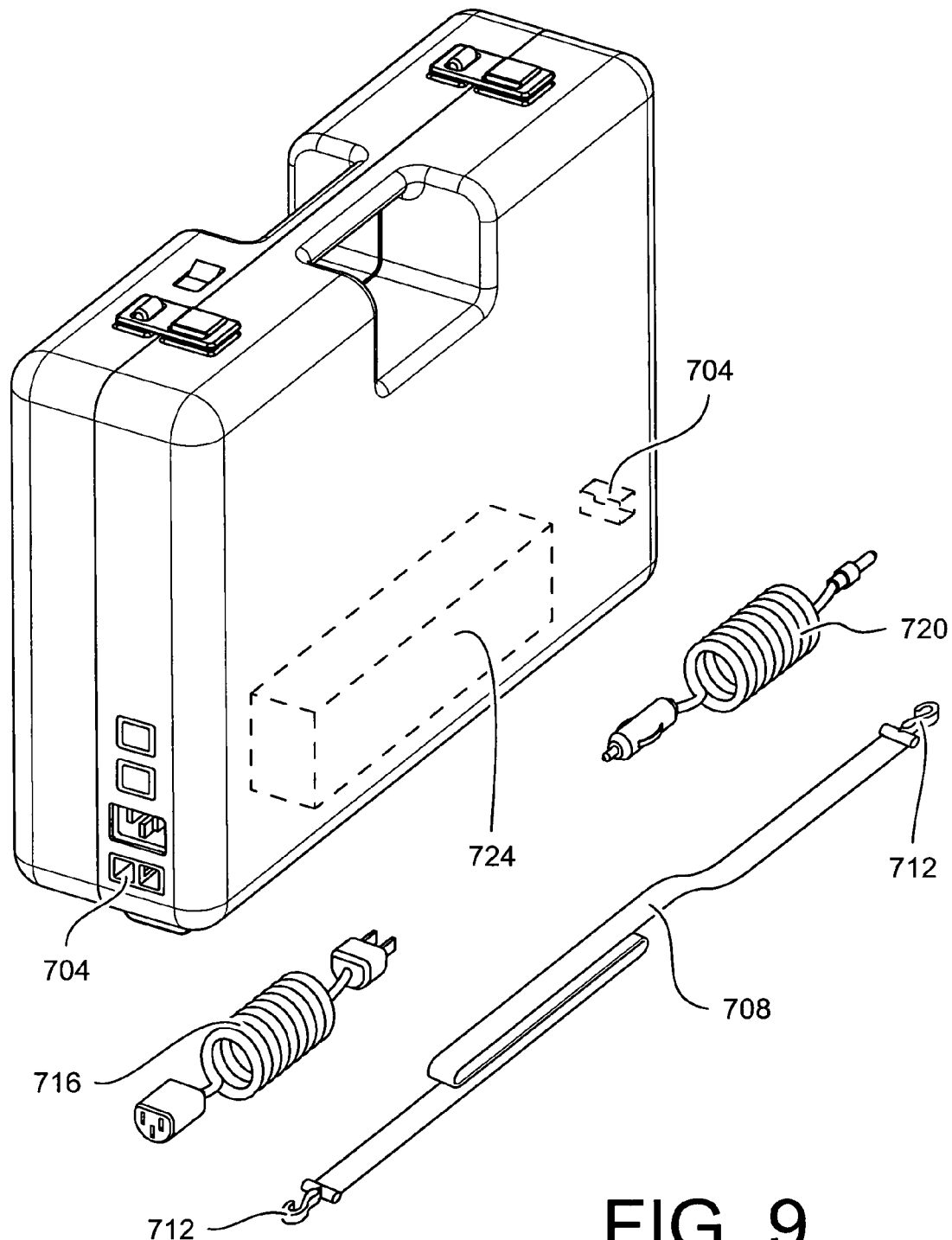
FIG. 9 shows accessories for use with the present invention.

As shown in FIGS. 1 and 9, the blanket warmer 100 has on its exterior surface a handle 120. The case assembly may be designed as a portable unit, or also as a securely mounted unit held in position by use of fasteners such as the attachment points 704. Additionally, the exterior surface of the entire unit may be decorated by manufacturer or have decals applied to it for the purposes of advertisement and/or identification. The attachment points 704 allow the clip-on attachment of an optional strap 708 by the use of attachment clips 712. This could also be useful for carrying the blanket warmer 100.

Also as shown in FIG. 9, the blanket warmer 100 can also have a storage area 724 located directly under it. Portions of FIG. 9 may be exaggerated for emphasis. This storage area can contain a converter 716 and lighter plug 720.

The blanket warmer 100 can also be equipped with mounting brackets for convenient wall storage when not in use. The blanket warmer 100 can also come in a variety of storage capacities, including but not limited to an embodiment suitable for heating horse blankets, as well as other large animals. The blanket warmer 100 can also be equipped with a variable-temperature thermostat, in communication with specialized temperature sensors, for allowing a user to customize a specific desired temperature. Further, the blanket warmer 100 can contain a power supply LED indicator which could be useful for showing whether or not the external electrical energy (such as either 10-volt wall outlet or 12-volt cigarette lighter plug) or battery is in use.

It is anticipated that various changes may be made in the arrangement and operation of the system of the present invention without departing from the spirit and scope of the invention, as depicted in the following claims.

What is claimed is:

1. A blanket warmer, comprising:
    a movable housing having upper and lower halves;
    a plurality of heating elements positioned within both upper and lower halves of the movable housing, where the heating elements are electrically connected to and powered by a power source;
    a hinge, integrally located within the movable housing, for providing a pivot point between the upper and lower halves;
    upper and lower liners, located within said upper and lower halves respectively, and in mechanical contact with the plurality of heating elements;
    a switch for enabling a user to selectively activate the blanket warmer;
    a two part latch having both mechanical and electrical properties, located on respective edges of the upper and lower halves; wherein
    the two part latch closes an electrical circuit when the movable housing is in a closed position, so that the plurality of heating elements can only become activated when the latch is in a closed position; and
    a thermostat for detecting when the heating elements should activate and deactivate.

2. The blanket warmer of claim 1, further comprising:
    the upper and lower halves when closed form an aperture suitable for warming and storing at least one blanket.

3. The blanket warmer of claim 1, wherein the blanket warmer is energized from one of an A/C electrical outlet, a DC converter, and a vehicle electrical system.

4. The blanket warmer of claim 1, wherein the movable housing forms a seat.

5. The blanket warmer of claim 1, further comprising:
    when in its closed position, the movable housing comes together to form a handle.

6. The blanket warmer of claim 5, further comprising:
    a storage area located opposite handle.

7. The blanket warmer of claim 6, wherein the storage area is configured to hold a converter and lighter plug.

8. The blanket warmer of claim 1, wherein the switch comprises a rocker switch.

9. The blanket warmer of claim 1, wherein the switch includes a light embedded therein.

10. The blanket warmer of claim 1, wherein the upper half is joined to the lower half by a full length hinge.

11. The blanket warmer of claim 1, further comprising:
    a respective thermostat coupled with each heating element, wherein each heating elements and its respective thermostats combine to form a wiring harness located within the upper and lower halves, respectively.

12. The blanket warmer of claim 1, further comprising:
    a temperature sensor configured to regulate a maximum temperature of the plurality of heating elements.

13. The blanket warmer of claim 1, wherein:
    the temperature sensor is a bi-metal sensor.

14. The blanket warmer of claim 1, wherein:
    the upper and lower liners transfer the heat from the heating elements uniformly to the blanket.

15. The blanket warmer of claim 1, wherein the upper and lower liners are composed of aluminum.

16. The blanket warmer of claim 1, wherein:
    the upper and lower liners are coated with a material suitable for transferring retaining heat.

17. The blanket warmer of claim 1, wherein:
    the upper and lower halves are composed of a high rigidity heat resistance plastic.

18. The blanket warmer of claim 1, wherein:
    the upper and lower halves are composed of fiberglass.

19. The blanket warmer of claim 1, wherein:
    the upper and lower halves are composed of acrylonitrile butadiene styrene.

20. The blanket warmer of claim 1, further comprising:
    a power supply indicator light, connected to the power source and visible from the external surface of the blanket warmer.

21. The blanket warmer of claim 1, further comprising:
    a fuse, located between the power supply and the heating elements, configured to determine when a current drawn by the heating elements is above a predetermined value.

22. The blanket warmer of claim 1, wherein:
    the movable housing is portable.

23. The blanket warmer of claim 1, wherein:
    the movable housing is mounted in position with fasteners.

24. The blanket warmer of claim 1, further comprising:
    attachment points for attaching of a clip-on strap.

25. The blanket warmer of claim 1, wherein:
    the movable housing has mounting brackets on an external surface thereof.

* * * * *